United States Patent [19]

VandenBerg

[11] Patent Number: Plant 7,315

[45] Date of Patent: Sep. 4, 1990

[54] CHRYSANTHEMUM PLANT NAMED LEONA

[75] Inventor: Cornelis P. VandenBerg, Salinas, Calif.

[73] Assignee: Yoder Brothers, Inc., Barberton, Ohio

[21] Appl. No.: 359,922

[22] Filed: May 31, 1989

[51] Int. Cl.[5] ..... A01H 5/00

[52] U.S. Cl. ..... -0t./74

[58] Field of Search ..... Plt./74.1, 822, 823, Plt./74

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Leona particularly characterized by its flat capitulum form, anemone capitulum type, bronze ray floret color, diameter across face of capitulum of up to 9 cm at maturity, with diameter of anemone cushion up to 3 cm.; uniform eight week photoperiodic flowering response to short days, peduncle length ranging form 10 to 25 cm on open, terminal sprays, and medium plant height when grown as a single stem spray cut mum.

3 Drawing Sheets

The present invention comprises a new and distinct cultivar of Chrysanthemum, botanically known as *Dendranthema grandiflora,* and referred to by the cultivar name Leona.

Leona, identified as 84-112003, was originated from a cross made by Cornelis P. VandenBerg in a controlled breeding program in Salinas, Calif., in 1983.

The female parent and the male parent of Leona were both unnamed seedlings, identified respectively as 78-20008 and 77-358001.

Leona was discovered and selected as one flowering plant within the progeny of the stated cross by Cornelis P. VandenBerg in August 1984, in a controlled environment in Salinas, Calif.

The first act of asexual reproduction of Leona was accomplished when vegetative cuttings were taken from the initial selection in October 1984, in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Leona are firmly fixed and are retained through successive generations of asexual reproduction.

Leona has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Leona, which, in combination, distinguish this Chrysanthemum as a new and distinct cultivar:

1. Flat capitulum form.
2. Anemone capitulum type.
3. Bronze ray floret color.
4. Diameter across face of capitulum up to 9 cm at maturity, with diameter of anemone cushion up to 3 cm.

5. Uniform eight week photoperiodic flowering response to short days.
6. Peduncle length ranging from 10 to 25 cm on open terminal sprays.
7. Medium plant height, requiring two long day weeks prior to short days to attain a flowered plant height of 100 to 110 cm for year-round flowerings.

The accompanying photographic drawings show typical inflorescence and leaf characteristics of Leona, with the colors being as nearly true as possible with illustrations of this type.

Sheet 1 is a color photograph of Leona grown as a single stem cut spray mum.

Sheet 2 is a black and white photograph of three views of the inflorescence of Leona.

Sheet 3 is a black and white photograph showing the upper and under sides of the leaves of Leona at three stages of development (mature, intermediate and immature).

Of the commercial cultivars known to the inventor, the most similar in comparison to Leona is Dramatic, disclosed in U.S. Plant Pat. No. 3,189. Reference is made to attached Chart A, which compares certain characteristics of Leona to the same characteristics of Dramatic.

Similar traits are ray floret color and diameter of capitulum. Leona is an anemone, while Dramatic is a daisy. Leona has longer peduncles, taller plant height and a shorter flowering response period. Dramatic frequently exhibits compounding of the spray formation, while Leona always has a terminal spray formation.

In the following description color references are made to The Royal Horticultural Society Colour Chart. The exact color of the ray florets of Leona is not represented in The R.H.S. Colour Chart, and the color values given are those closest to the actual color of Leona. The color values were determined on plant material grown in Salinas, Calif. on July 15, 1988.

Classification:

*Botanical.*—*Dendranthema grandiflora,* cv Leona.

*Commercial.*—Anemone cut spray mum.

INFLORESCENCE

A. Capitulum:

*Form.*—Flat.

*Type.*—Anemone.

*Diameter across face.*—Up to 9 cm at maturity, with diameter of anemone cushion up to 3 cm.

B. Corolla of Ray Florets:

*Color (general tonality from a distance of three meters).*—Bronze.

*Color (upper surface).*—16A, with an overcast of 163A.

*Color (under surface).*16B.

*Shape.*—Flat, straight, oblong.

C. Corolla of Disc Florets:

*Color (mature).*—16A, tinged with 163A.

*Color (immature).*—16A, tinged with 163A and a slight green overcast.

D. Reproductive organs:

*Androecium.*—Present on disc florets only; moderate pollen.

*Gynoecium.*—Present on both ray and disc florets.

PLANT

A. General Appearance:

*Height.*—Medium; 100 to 110 cm as a single stem cut mum with two long day weeks prior to short days.

B. Foliage:

*Color (upper surface).*—147A.

*Color (under surface).*—147B.

*Shape.*—Deeply lobed and serrated.

CHART A

COMPARISON OF LEONA and DRAMATIC

| Cultivar | LEONA | DRAMATIC |
|---|---|---|
| Ray floret color | Bronze | Bronze |
| Capitulum form and type | Flat anemone | Flat daisy |
| Spray formation | Terminal | Terminal to compound |
| | 10 to 25 cm peduncles | 5 to 12 cm peduncles |
| Diameter across face of capitulum | up to 9 cm | up to 9 cm |
| Plant height | Medium | Short |
| Flowering response period | 8 weeks | 9 weeks |

Comparisons Made of Plants Grown As Single Stem Spray Cut Mums In Salinas, California

I claim:

1. A new and distinct plant of Chrysanthemum named Leona, as described and illustrated.

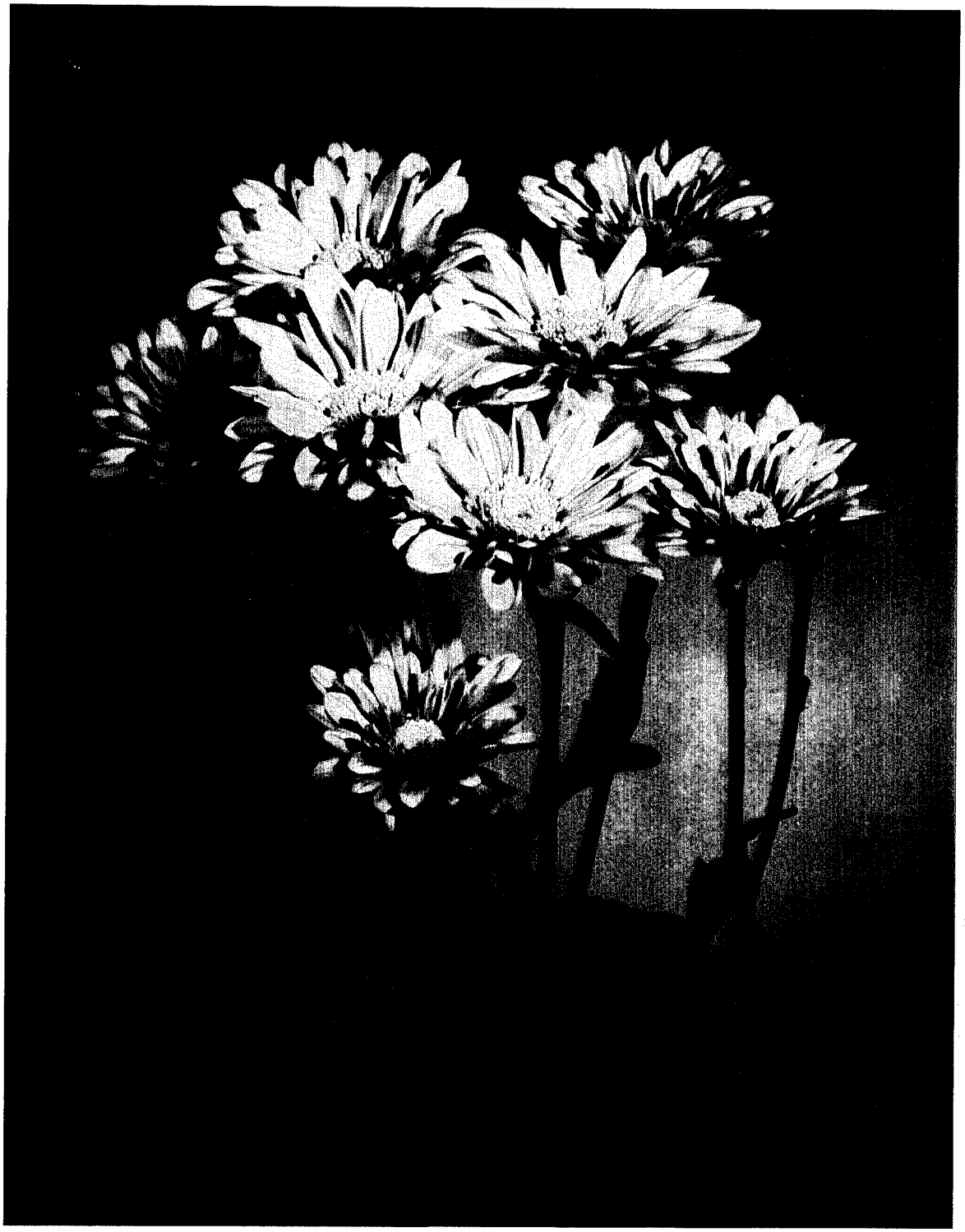

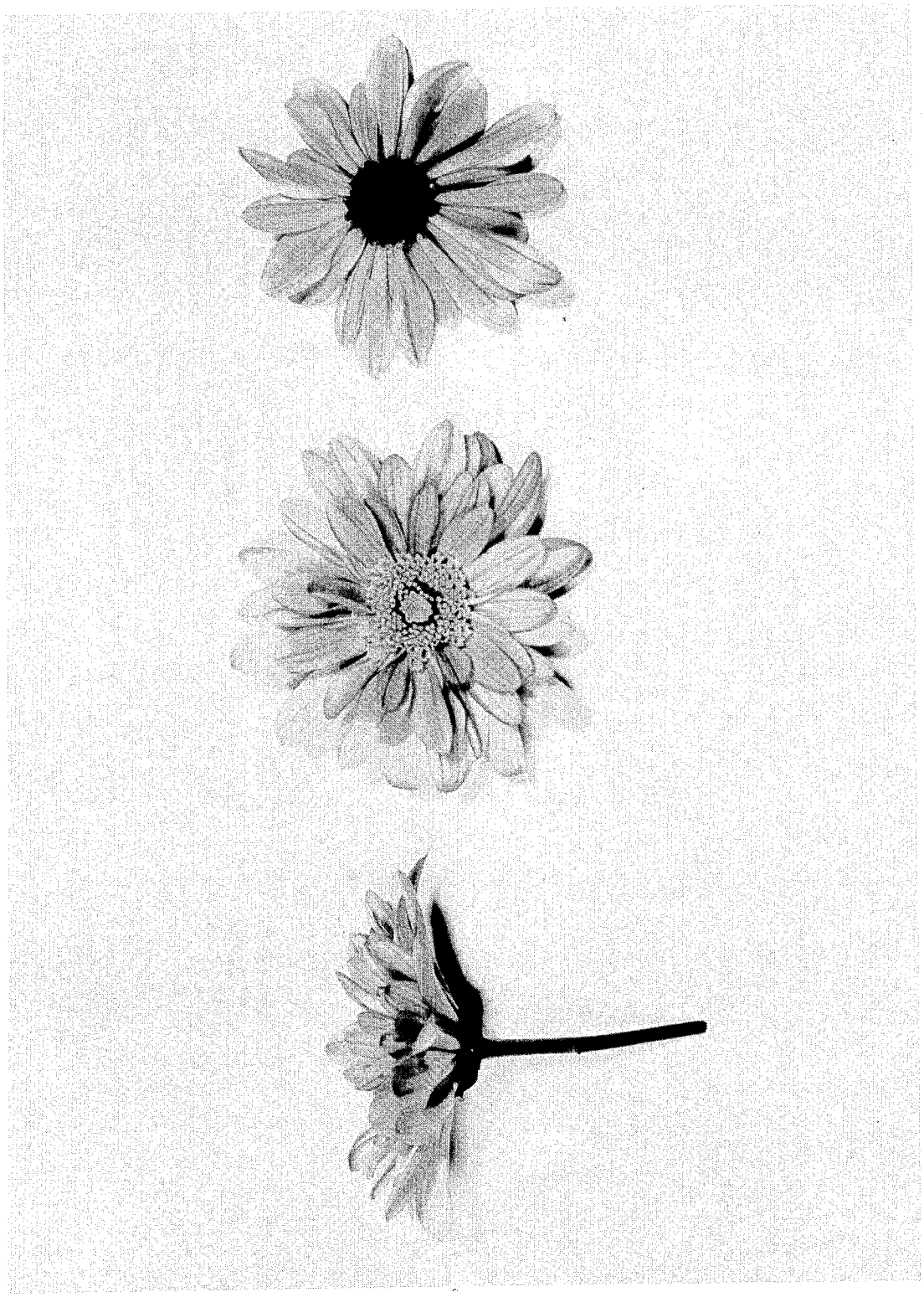

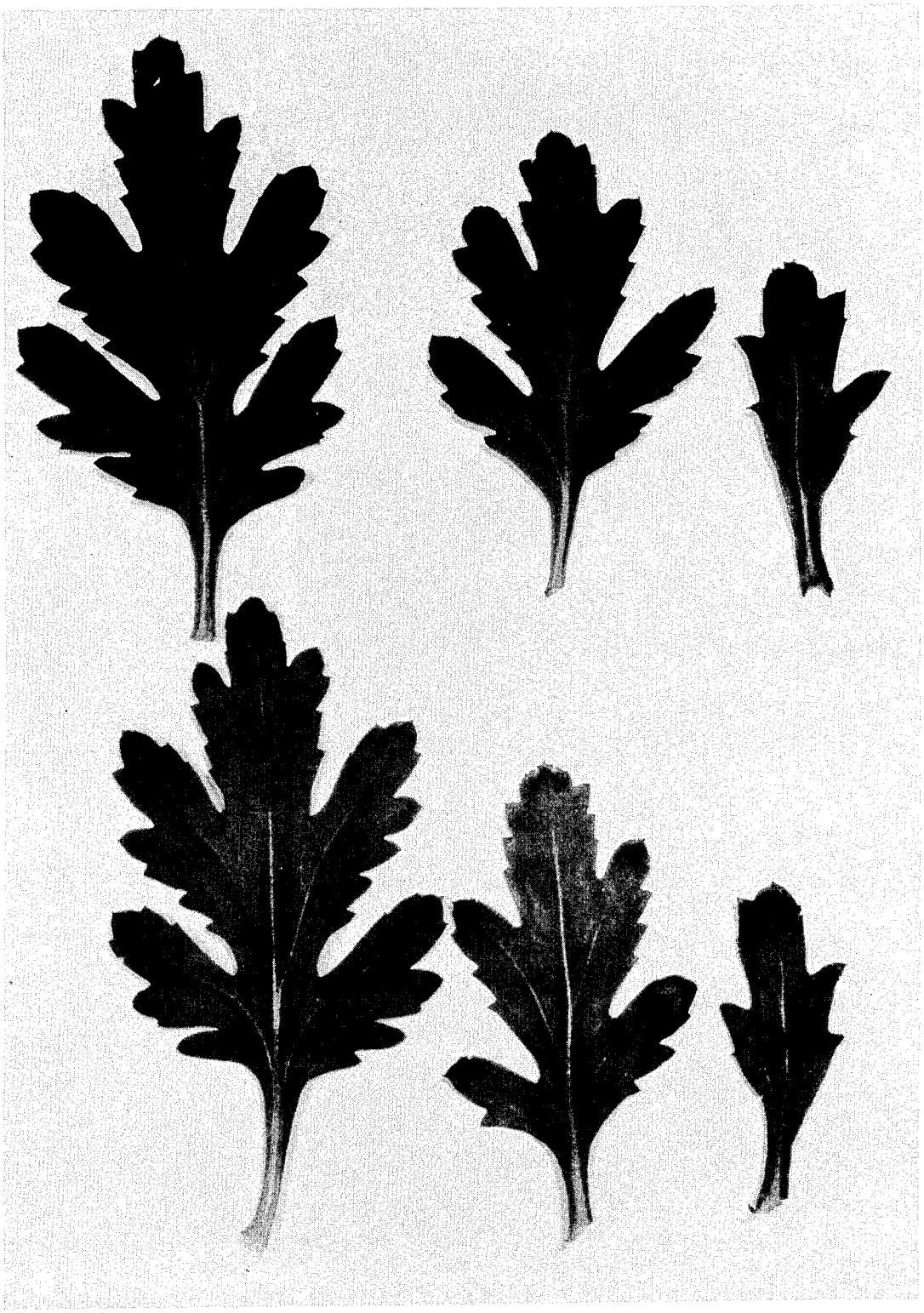

* * * * *